United States Patent
Kuo et al.

(10) Patent No.: US 9,962,487 B2
(45) Date of Patent: May 8, 2018

(54) AUTOMATIC SENSING AND WARNING DEVICE FOR PLACING INTRAVENOUS DRIP

(71) Applicants: CATHAY GENERAL HOSPITAL, Taipei (TW); TZU-CHI UNIVERSITY OF SCIENCE AND TECHNOLOGY, Hualien (TW)

(72) Inventors: Ming-Chuan Kuo, Taipei (TW); Zu-Chun Lin, Hualien (TW); Chia-Hui Chu, Taipei (TW); Ping-I Li, Taipei (TW); Chia-Liang Lu, New Taipei (TW)

(73) Assignees: CATHAY GENERAL HOSPITAL, Taipei (TW); TZU-CHI UNIVERSITY OF SCIENCE AND TECHNOLOGY, Hualien (TW)

( * ) Notice: Subject to any disclaimer, the term of this patent is extended or adjusted under 35 U.S.C. 154(b) by 0 days. days.

(21) Appl. No.: 15/674,529

(22) Filed: Aug. 11, 2017

(65) Prior Publication Data
US 2018/0050152 A1  Feb. 22, 2018

(30) Foreign Application Priority Data
Aug. 19, 2016 (TW) .............................. 105126554 A

(51) Int. Cl.
*G08B 13/14* (2006.01)
*A61M 5/168* (2006.01)
(Continued)

(52) U.S. Cl.
CPC ....... *A61M 5/16836* (2013.01); *A61B 5/0215* (2013.01); *A61B 5/04* (2013.01); *A61M 5/1689* (2013.01); *A61M 2205/18* (2013.01)

(58) Field of Classification Search
CPC .. A61M 5/14; A61M 5/16836; A61M 5/1689; A61M 2205/18; A61M 2205/60;
(Continued)

(56) References Cited

U.S. PATENT DOCUMENTS 5,822,544 A * 10/1998 Chaco ................... G06F 19/327
340/286.07
7,821,410 B2 * 10/2010 Higashionji ............... B41J 3/44
340/572.1

(Continued)

*Primary Examiner* — Van Trieu
(74) *Attorney, Agent, or Firm* — Leong C. Lei

(57) ABSTRACT

An automatic sensing and warning device for placing an intravenous drip includes a transmitter unit, a blocking unit, a receiver unit, and a fixing device. The transmitter unit is attachable to an injection site on a patient's hand and is operable to transmit an identification signal. The receiver unit is arranged on the blocking unit and includes a drive circuit and a warning device. The fixing device supports the blocking unit and the receiver unit on the intravenous drip pole. The RF receiver is set at a predetermined vertical distance from a drip chamber and areas above and below the RF receiver are respectively defined as dangerous and safe areas. When the injection site is spaced from the drip chamber by a distance shorter than the predetermined distance, the RF receiver receives the identification signal from the RF transmitter and the drive circuit activates the warning device to issue warnings.

8 Claims, 12 Drawing Sheets

(51) Int. Cl.
*A61B 5/04* (2006.01)
*A61B 5/0215* (2006.01)

(58) Field of Classification Search
CPC .. A61M 2205/168; A61M 2205/16831; A61M 2205/172; A61M 2205/1723; G08B 13/14; G08B 21/24; G08B 21/245; G08B 26/00; G08B 26/001; G08B 26/004; G08B 26/007; A61B 5/00; A61B 5/02007; A61B 5/0205; A61B 5/021; A61B 5/0215; A61B 5/02152; A61B 5/024; A61B 5/04; A61B 5/04001; G06Q 50/22; G06Q 50/24
See application file for complete search history.

(56) References Cited

U.S. PATENT DOCUMENTS

| | | | |
|---|---|---|---|
| 7,982,623 B2* | 7/2011 | Higashionji | B41J 3/44 340/572.1 |
| 9,235,977 B2* | 1/2016 | Deutsch | G08B 21/245 |
| 9,642,967 B2* | 5/2017 | Ribble | G06F 19/3418 |
| 2008/0303638 A1* | 12/2008 | Nguyen | G06F 19/3462 340/10.42 |
| 2017/0224561 A1* | 8/2017 | Ribble | A61G 7/018 |

* cited by examiner

AUTOMATIC SENSING AND WARNING DEVICE FOR PLACING INTRAVENOUS DRIP

(a) TECHNICAL FIELD OF THE INVENTION

The present invention relates generally to a warning device, and more particularly to an automatic sensing and warning device for placing intravenous drip.

(b) DESCRIPTION OF THE PRIOR ART

Peripheral intravenous infusion allows for quick and precise delivery of medication, electrolyte, and nutrition for therapy of patients and is commonly medical treatment for inpatients. Care and direction of intravenous infusion is an important daily routine operation for nurses.

Investigation of hospital practices indicate as high as 96% of patients need intravenous infusion involved therapy and as high as 47% of the emergency calls are applied due to problems associated with intravenous infusion. Among these problems, most are associated with jamming caused by reverse flow of blood resulting from insufficient height of intravenous drip bottle, which amounts to 45.5%.

Further, according to statistics provided in related studies, around 80-90% of inpatients require intravenous infusion involved treatment and the chance of reverse blood flow and jamming is around 8.2-33.1%. Apparently, reverse blood flow and jamming is one of the most common clinic issues. When reverse blood flowing occurs in a peripheral vein, the nurses has to frequently answer the calling and move between the sickbeds and the nursing station for handling the issue and this increase the loading of the nurses and may unexpectedly interrupt certain medical caring in process. If jamming occurs due to no timely handling, then removal and re-insertion wound be necessary and this causes pains of the patient and reduces the degree of satisfaction of the medical caring, and may even cause waste of medical resources. In addition, this might jeopardize the patient's safety for immediate treatment may not be available for blood vessels that are hard for such injection.

Directions for caring of intravenous infusion that are practiced by the nurses of modern hospitals are generally based on oral instruction or written guide. Generally speaking, it is suggested the injection site must be lower than the intravenous drip bottle and the vertical distance between the height of the intravenous drip bottle and the injection site must be kept for at least 75 to 90 centimeters. In case of reverse blood flow of veins, the injection site must be first lowered down and the intravenous drip pole be heightened. And, request must be made for help with nurses.

According to statistics, 22.5% of the patients that take intravenous infusion therapy must suffer re-insertion due to unexpected removal of the needle, among which around 8.2% to 33.1% are due to jamming caused by reverse blood flow resulting from insufficient height of intravenous drop bottle. Insufficiency of intravenous drip bottle height is often related to non-temporary movement or lifting of the patient and is caused by artery pressure. Vein reverse blood flow may occur only when rising for a period exceeding for a predetermined interval such as 10 seconds.

Prevention of vein reverse blood flow is generally poor and reasons are as follows.

(1) No clear indication of height reference is provided for the patient to follow.

(2) The capability of recognition and comprehension of a patient or an attendant is insufficient.

(3) The memory of human beings is generally limited and the patient or the attendant may forget important instructions.

(4) No warning device is provided for reminding of the height of the intravenous drip height.

Prior art documents are known, such as Taiwan Utility Models M525194 and M524723, and also Taiwan Utility Model M509047, which shows, in FIG. 1 thereof, a device that has an end to which a retaining needle is mounted and an end connected to a T connector. This is a disposable consumable and would thus increase the medical caring cost, making it hard to commercialize.

Thus, it is desired to provide a high-tech smart warning device for providing automatic warning and mature techniques of radio frequency are used to reduce cost in order to provide an automatic sensing and warning device for placing intravenous drip that features dual conditions of height and time. When a vertical distance between an injection site of a patient and a drip chamber is less than a predetermined range and such a condition remains for a time period that exceeds a predetermined number of seconds, warning in the form of audio sound and lighting may be activated to remind, in a real-time manner, the patient to lower down the injection site in order to prevent vein reverse blood flow and jamming The present invention aims to provide a technical solution that overcomes the above problems.

SUMMARY OF THE INVENTION

An objective of the present invention is to provide an automatic sensing and warning device for placing intravenous drip, which activates a warning device to issue a warn when a vertical distance between an injection site of a patient and a drip chamber is less than a predetermined distance, in order to remind the patient to lower down the injection site or to raise the intravenous drip pole for preventing reverse flow and protecting the patient against vein reverse blood flow and jamming To achieve the above objective, the present invention comprises a transmitter unit, a blocking unit, a receiver unit, and a fixing device, wherein the transmitter unit comprises an encoder circuit and a radio frequency (RF) transmitter that are electrically connected, the encoder circuit comprising a first switch and an encoder integrated circuit (IC) for setting an identification signal of the transmitter unit, wherein the RF transmitter is operable to transmit out the identification signal and the transmitter unit is adapted to attach to an injection site on a hand of a person; the blocking unit comprises a blocking member and a seat, the blocking member being made of a metallic material and mounted on the seat, the seat being adapted to attach to an intravenous drip pole to be substantially perpendicular to the intravenous drip pole, so as to block the identification signal transmitted from the RF transmitter located in one given range of the seat; the receiver unit is mounted to the blocking unit, the receiver unit comprising an RF receiver, a decoder circuit, at least one drive circuit, and at least one warning device, the RF receiver being operable to receive the identification signal transmitted from the RF transmitter located in another one given range of the seat, the decoder circuit being coupled to the RF receiver, the drive circuit being coupled to the decoder circuit, the warning device being coupled to the drive circuit, the decoder circuit comprising a second switch and a decoder IC; and the fixing device supports the blocking unit and the receiver unit and is adapted to mount to the intravenous drip pole.

Thus, the RF receiver is set at a predetermined distance (such as 90 centimeters) from the drip chamber to define a dangerous zone and a safe zone that are respectively located above and below the RF receiver. When a vertical distance between an injection site of a patient and a drip chamber is less than the predetermined distance, the RF receiver is capable to receive the identification signal transmitted from the RF transmitter, and the drive circuit activates the warning device to issues warnings, such as audio sounds and lighting, to provide a reminder for lowering down the injection site or lifting up the intravenous drip pole in order to prevent an excessively short vertical distance between the injection site of the patient and the intravenous drip that might cause reverse flowing and to protect the patient from vein reverse blood flow and jamming caused by for example the patient raising the hand.

Advantageous efficacies of the present invention are reducing the chance of re-insertion of a retaining needle, improving positive attendant-patient relationship, and lowering down the time and cost of medical caring.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
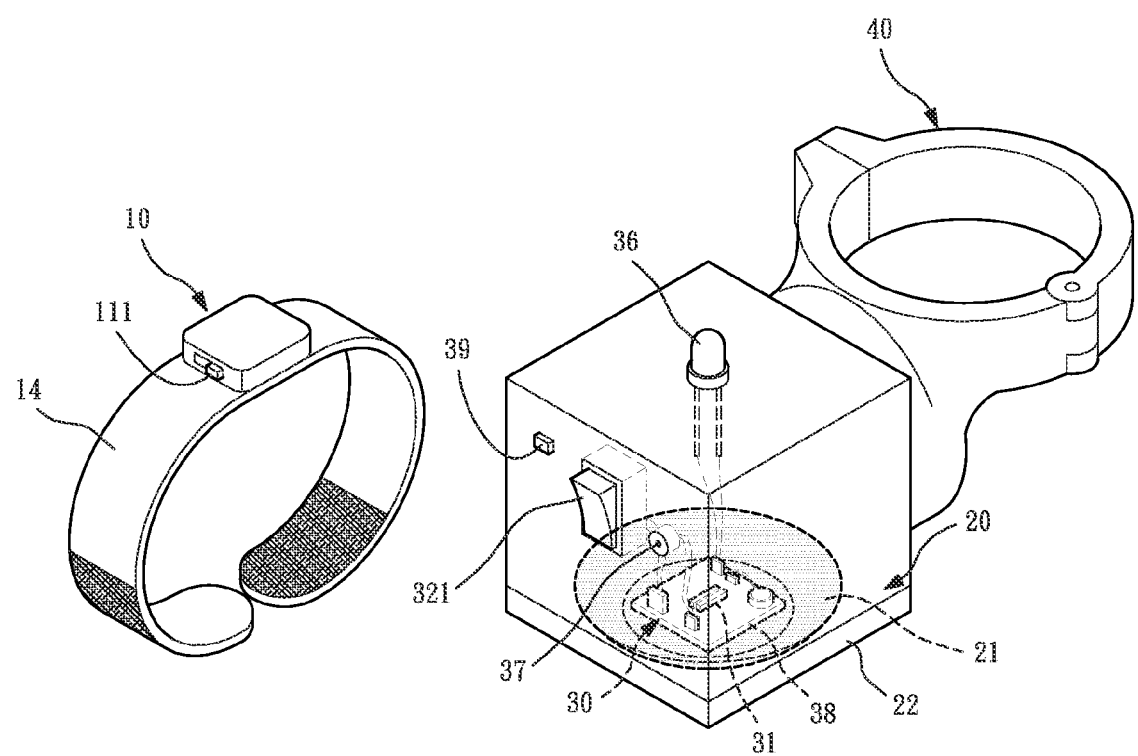
FIG. 1 is a perspective view of the present invention.
Figure 2:
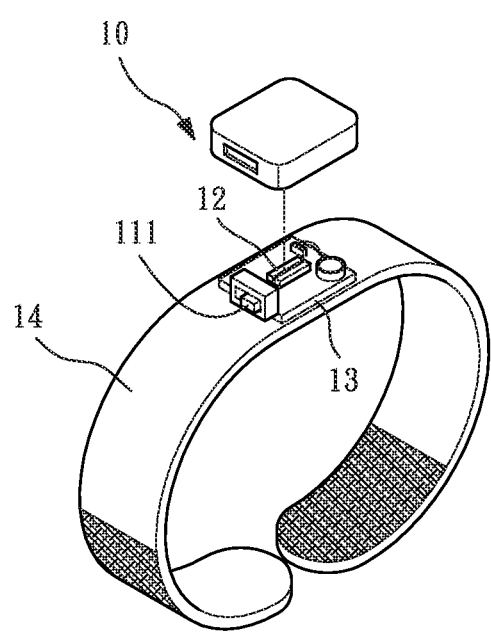
FIG. 2 is an exploded view of a transmitter unit of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The scientific basis of the present invention will be introduced first. With the progress of science and technology, measures making use of wireless transmission to provide assistance to caring operations are now prevailing. The wireless transmission measures generally rely on electromagnetic waves as a data transmission medium. Electromagnetic waves that are used to transmit data are classified in three categories, which are radio frequency (RF), microwave, and infrared. The characteristics of these three categories are different. The radio frequency involves a sensing range from 30 Mhz to 1 GHz and is omni-directional radiation and is generally applicable to positioning sensing. The microwave involves a sensing range from 1 GHz to 100 GHz and is directional radiation and is generally applicable to point to point sensing. The infrared involves a sensing range from 3×1011 to 2×1014 Hz and is point to point or multiple point among areas and is generally applicable to sensing article moving among areas. The radio frequency has power of transmission better than the other two and is generally not directional so as to be used in positioning sensing and also used in measuring distances.

Common RF applications in daily living include radio broadcast channels (AM and FM channels), household wireless network communication, transmission of TV signals, and mobile audio communication. RF is a common technique applicable to daily living. In medical field, the commonly used RF technique is used in combination with processing achieved with microchips to provide radio frequency identification (RFID) techniques, of which the principle is an RF signal is transmitted and the RF signal carries and transmits data necessary for identification. The necessary data are transmitted to a reader and application systems in the microchips and middleware carry out data transformation, reading, and use in order to achieve the purposes of positioning and identification.

Referring to FIGS. 1-10, the present invention comprises a transmitter unit 10, a blocking unit 20, a receiver unit 30, and a fixing device 40. Details will be provided below.

The transmitter unit 10 comprises an encoder circuit 11 and a radio frequency (RF) transmitter 12 electrically connected to each other. The encoder circuit 11 comprises a first switch 111 and an encoder integrated circuit (IC) 112 for setting an identification signal of the transmitter unit 10. The RF transmitter 12 is operable to transmit out the identification signal. The transmitter unit 10 is adapted to attach to an injection site on a hand of a patient.

The blocking unit 20 comprises a blocking member 21 and a seat 22. The blocking member 21 is made of a metallic material and is mounted on the seat 21. The seat 21 is mountable to an intravenous drip pole 90 and is generally perpendicular to the intravenous drip pole 90. The identification signal transmitted by the RF transmitter 12 located in a range of the seat 22 will be blocked.

The instant embodiment is such that the transmission of the identification signal made by the RF transmitter 12 at a location below the seat 22 will be blocked.

The receiver unit 30 is mounted on the blocking unit 20. The receiver unit 30 comprises a RF receiver 31, a decoder circuit 32, at least one drive circuit, and at least one warning device. The RF receiver 31 receives the identification signal transmitted from the RF transmitter 12 located in another range of the seat 22. The decoder circuit 32 is coupled to the RF receiver 31. The drive circuit is coupled to the decoder circuit 32. The warning device is coupled to the drive circuit. The decoder circuit 32 comprises a second switch 321 and a decoder IC 322.

The fixing device 40 is provided for receiving and carrying the blocking unit 20 and the receiver unit 30 and is mounted to the intravenous drip pole 90.

In one structure example, the encoder circuit 11 and the RF transmitter 12 of the transmitter unit 10 are mounted on a first circuit board 13.

In one structure example, the transmitter unit 10 is mounted to a hand ring 14 that is provided with hook and hoop fastening strips in order to allow the hand ring 14 to attach the transmitter unit 10 to the injection site of the hand of the patient.

In one structure example, the blocking member 21 comprises a piece of disk-shaped or bowl-shaped tin foil.

Figure 9:
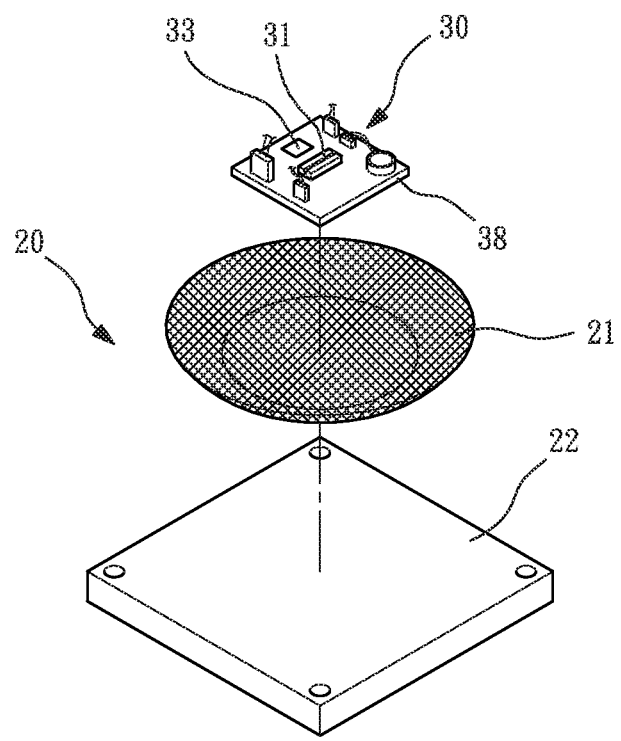
FIG. 9 is a schematic view showing a blocking member according to another embodiment of the present invention.

Referring to FIG. 9, in one structure example, the blocking member 21 comprises a disk-shaped metal net, such as copper and iron.

In one structure example, the decoder circuit 32 is coupled to a single-chip 33, and the single-chip 33 comprises a time delay module, which is operable for a delay of time (such as 10 seconds) in issuing a drive signal to the drive circuit, so as to delay driving the warning device.

In one structure example, the drive circuit comprises a light indication drive circuit 34 and a sound warning drive circuit 35. The light indication drive circuit 34 is electrically connected to a light emitter 36, such as a light emitting diode (LED). The sound warning drive circuit 35 is electrically connected to a buzzer 37.

In one structure example, the RF receiver 31, the decoder circuit 32, and the drive circuit of the receiver unit 30 are mounted on a second circuit board 38.

In one structure example, the fixing device 40 comprises a C-clip.

Figure 3:
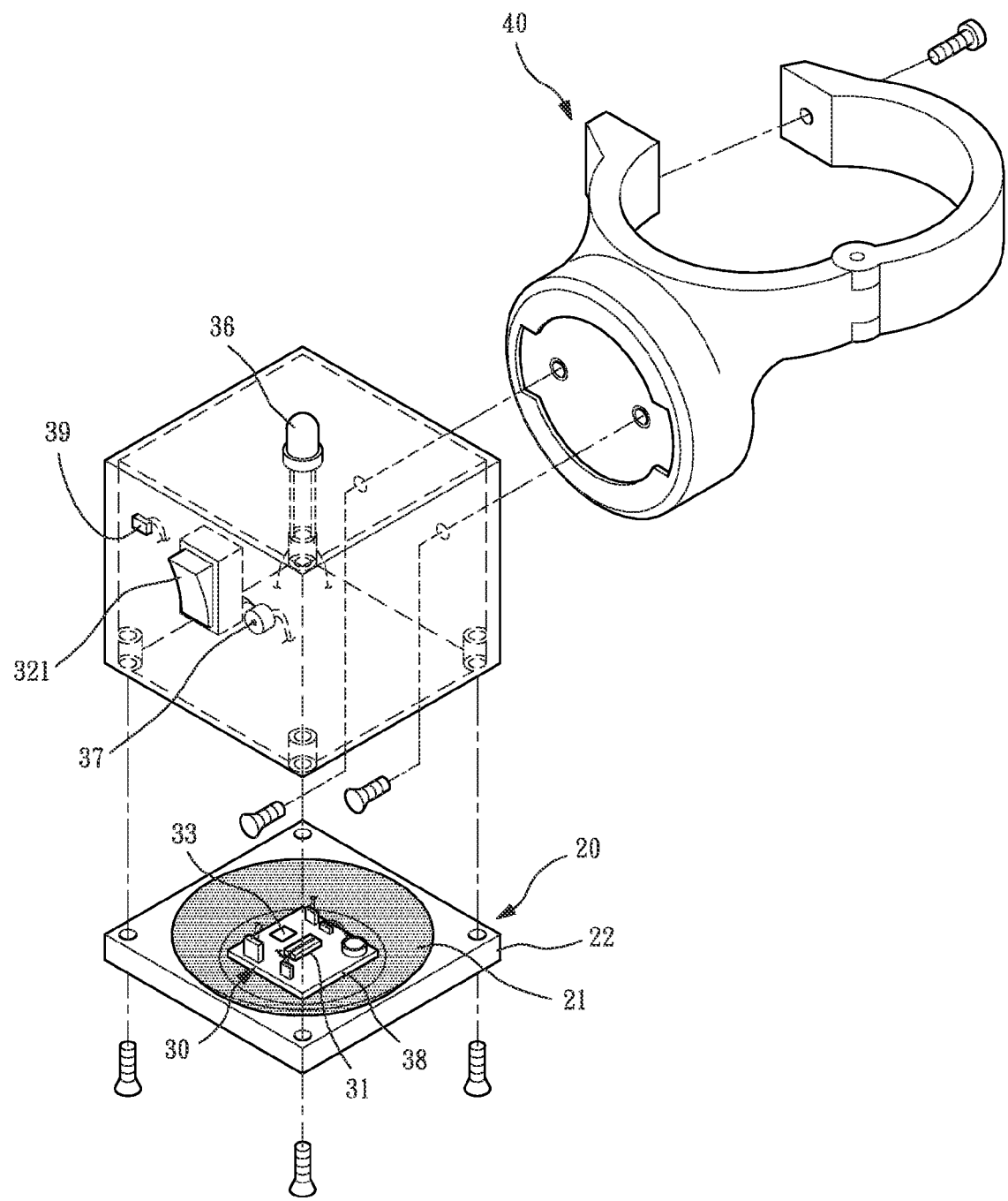
FIG. 3 is a perspective view showing, in an exploded form, a blocking unit, a receiver unit, and a fixing unit of the present invention.
Figure 4:
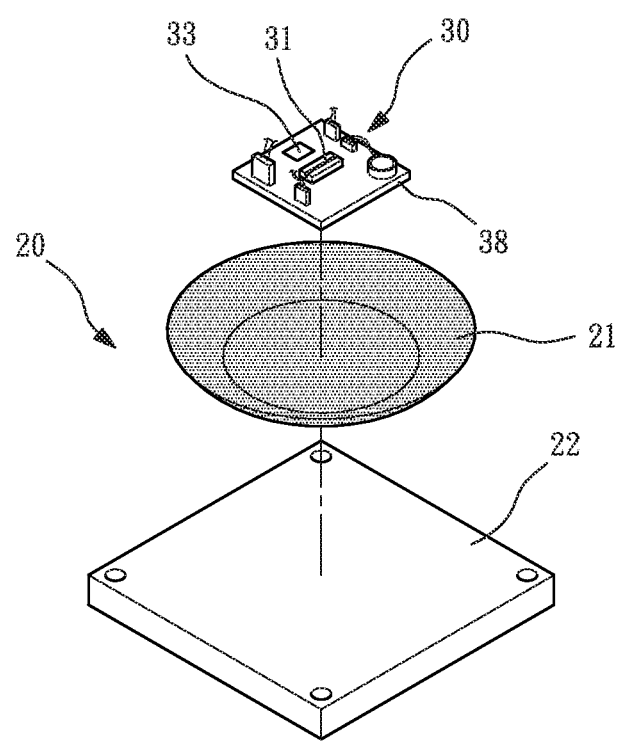
FIG. 4 is an exploded view of the blocking unit of the present invention.
Figure 5:
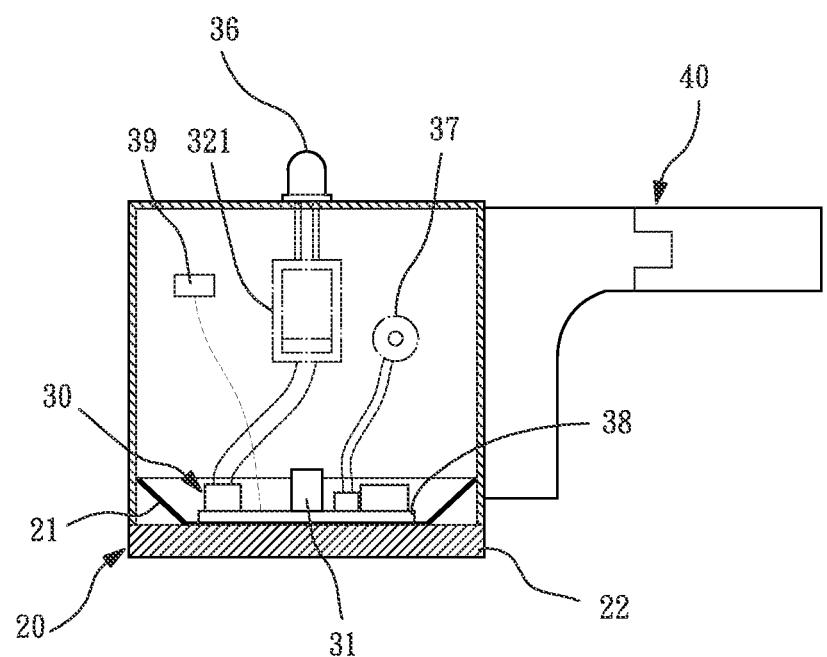
FIG. 5 is a cross-sectional view showing the blocking unit, the receiver unit, and the fixing unit of the present invention in an assembled form.
Figure 6:
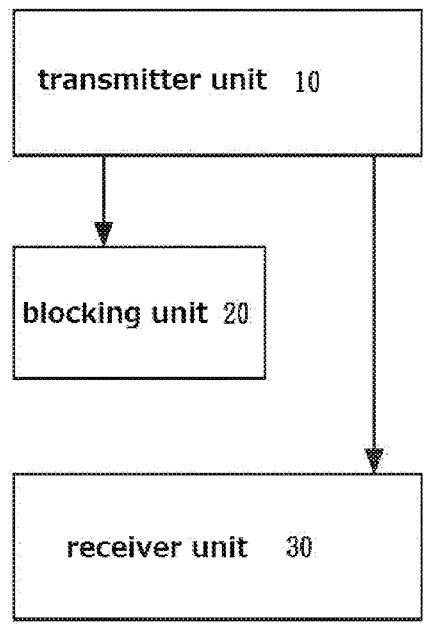
FIG. 6 is a block diagram showing a main structure of the present invention.
Figure 7:
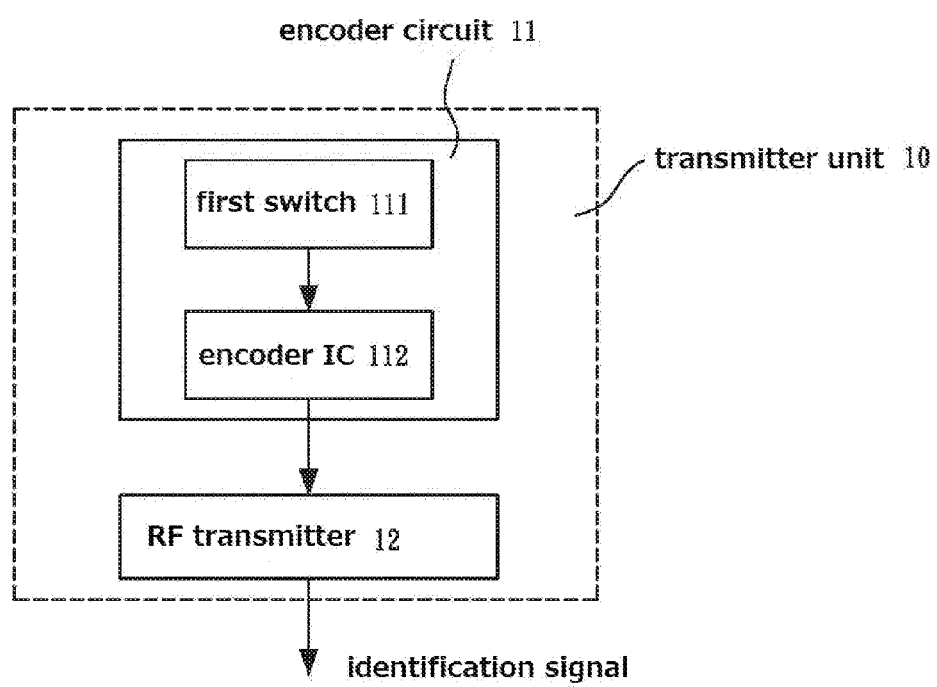
FIG. 7 is a block diagram of the transmitter unit of the present invention.
Figure 8:
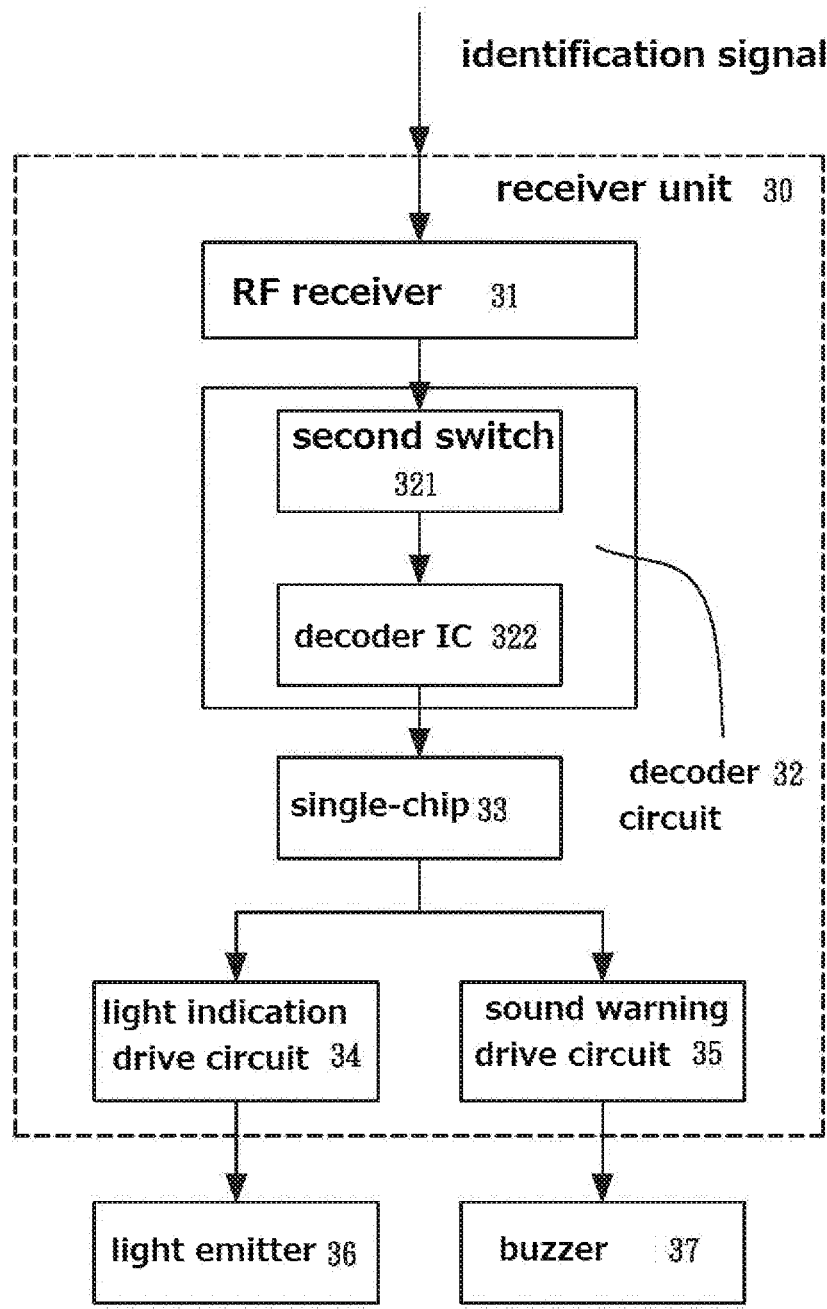
FIG. 8 is a block diagram of the receiver unit of the present invention.

Referring to FIGS. 1, 3, and 5, in one structure example, the receiver unit 30 comprises a shut-down switch 39, which is operable to cut off a single transmission circuit of the receiver unit 30.

The above provides a description to the structure of the present invention. The following provides a description to the components of the present invention and assemblies thereof, followed by a description concerning applications, features, and advantages of the present invention.

Figure 10:
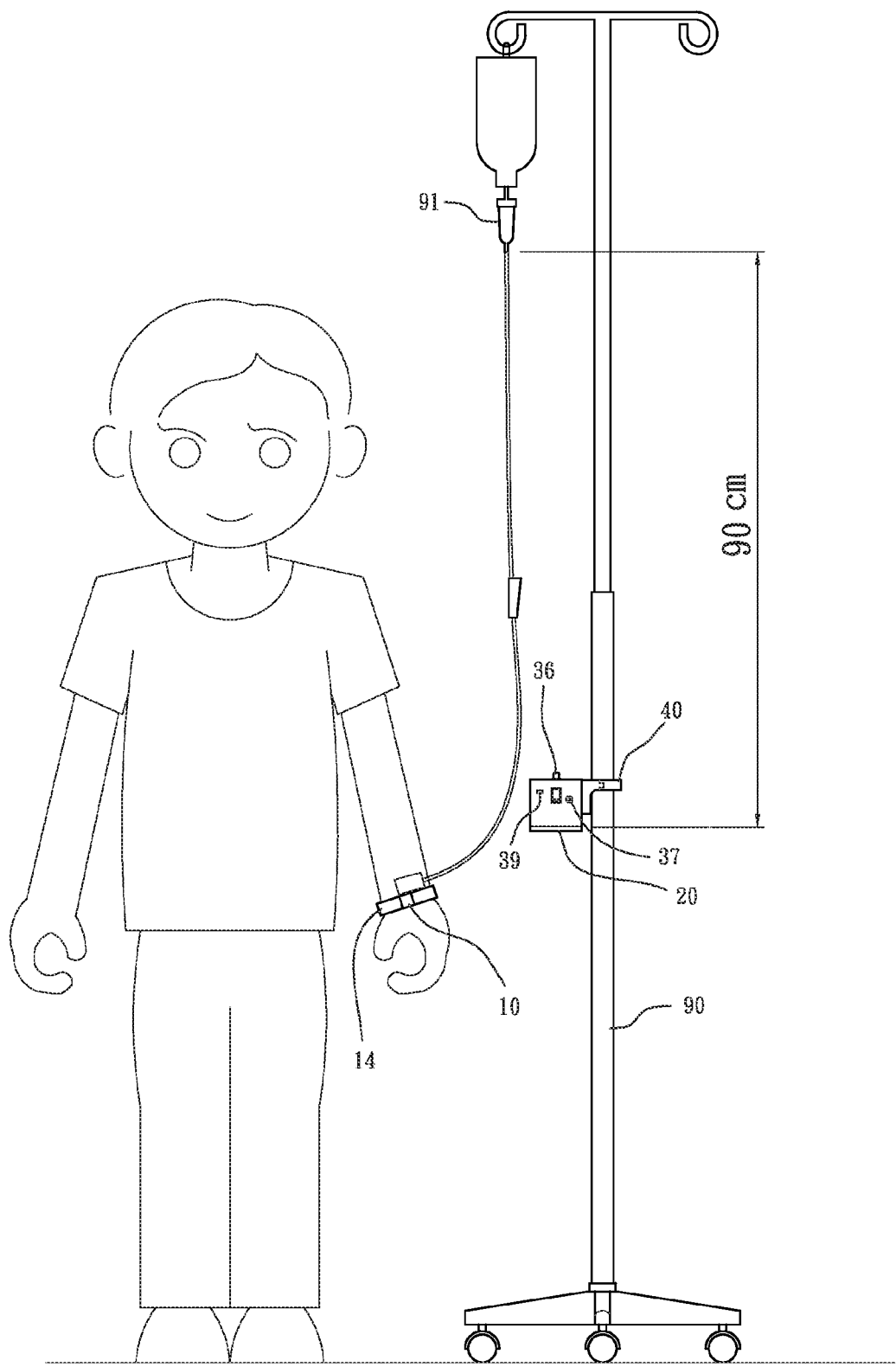
FIG. 10 is a schematic view illustrating an application in which the present invention does not issues a warning.
Figure 11:
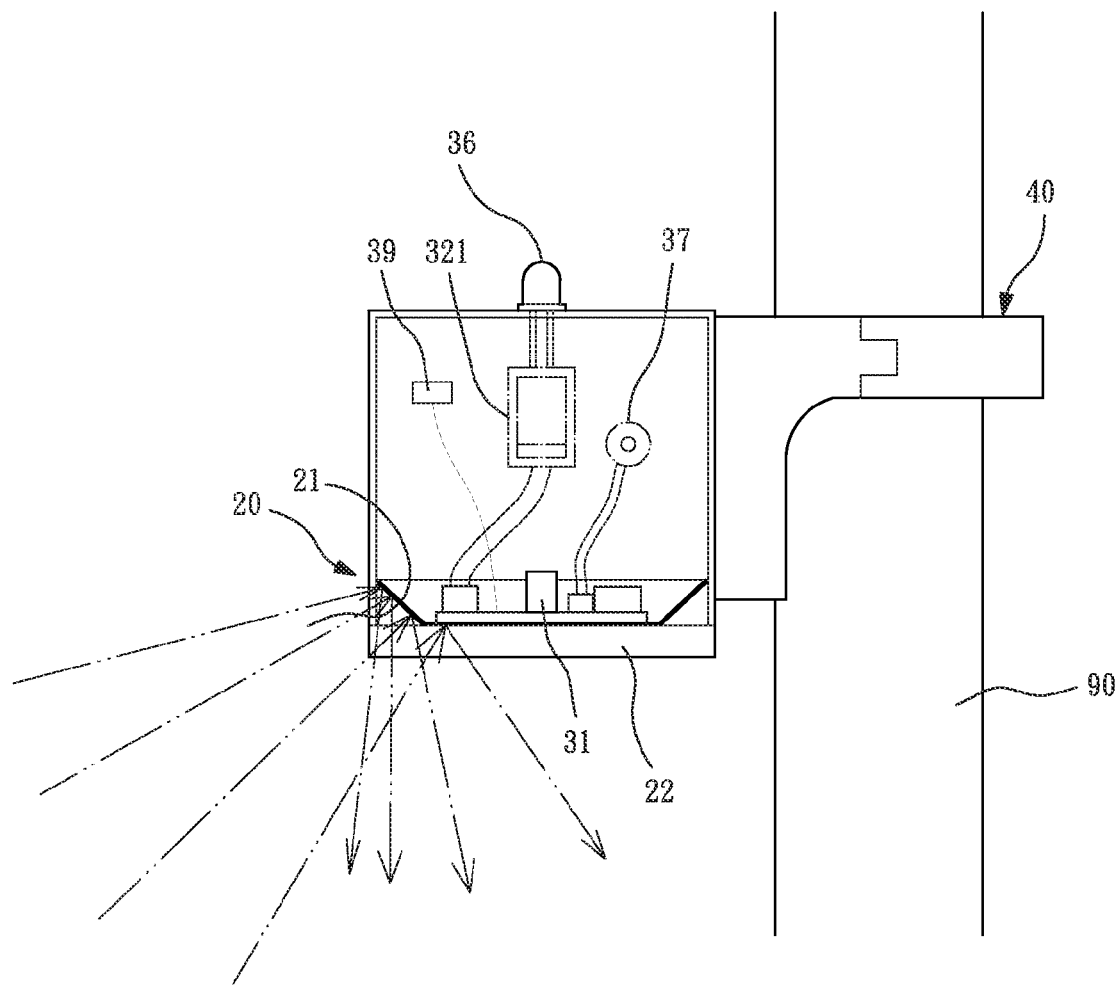
FIG. 11 is a schematic view illustrating an identification signal transmitted from an RF transmitter is blocked by the blocking member.

Referring to FIGS. 10 and 11, through moving the fixing device 40 to a desired location, the RF receiver 31 can be set at a desired distance (such as 90 centimeters) from the drip chamber 91 and thus, the area above the RF receiver 31 is a dangerous zone, while the area below the RF receiver is a safe zone.

The drawings show the injection site of the patient is located in the safe zone below the RF receiver 31, wherein the identification signal transmitted from the RF transmitter 12 is blocked by the blocking member 21 so that the light emitter 36 and the buzzer 37 do not generate warnings, indicating the patient's injection is in a normal condition.

Figure 12:
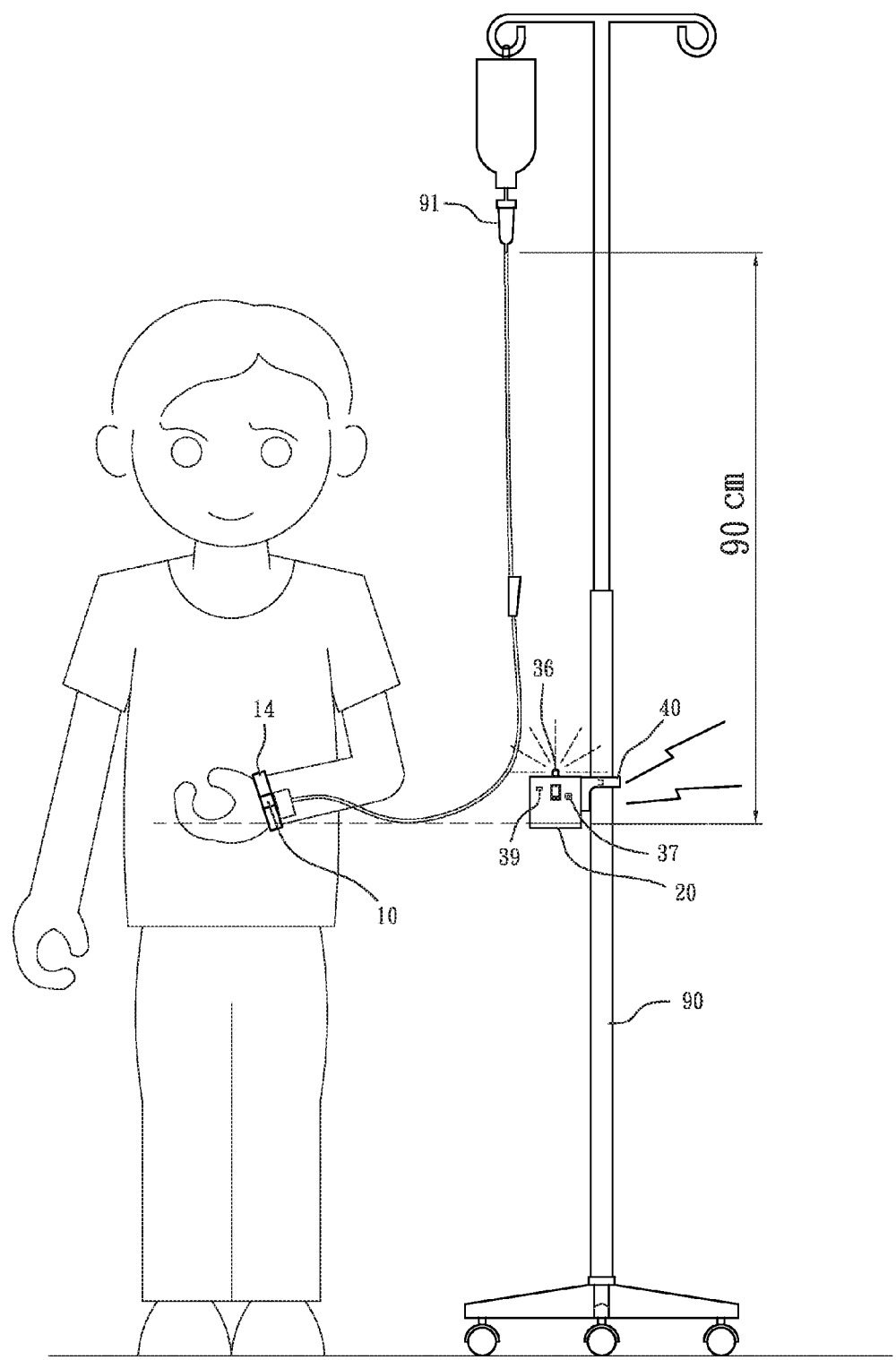
FIG. 12 is a schematic view illustrating an application in which the present invention does not issues a warning.
Figure 13:
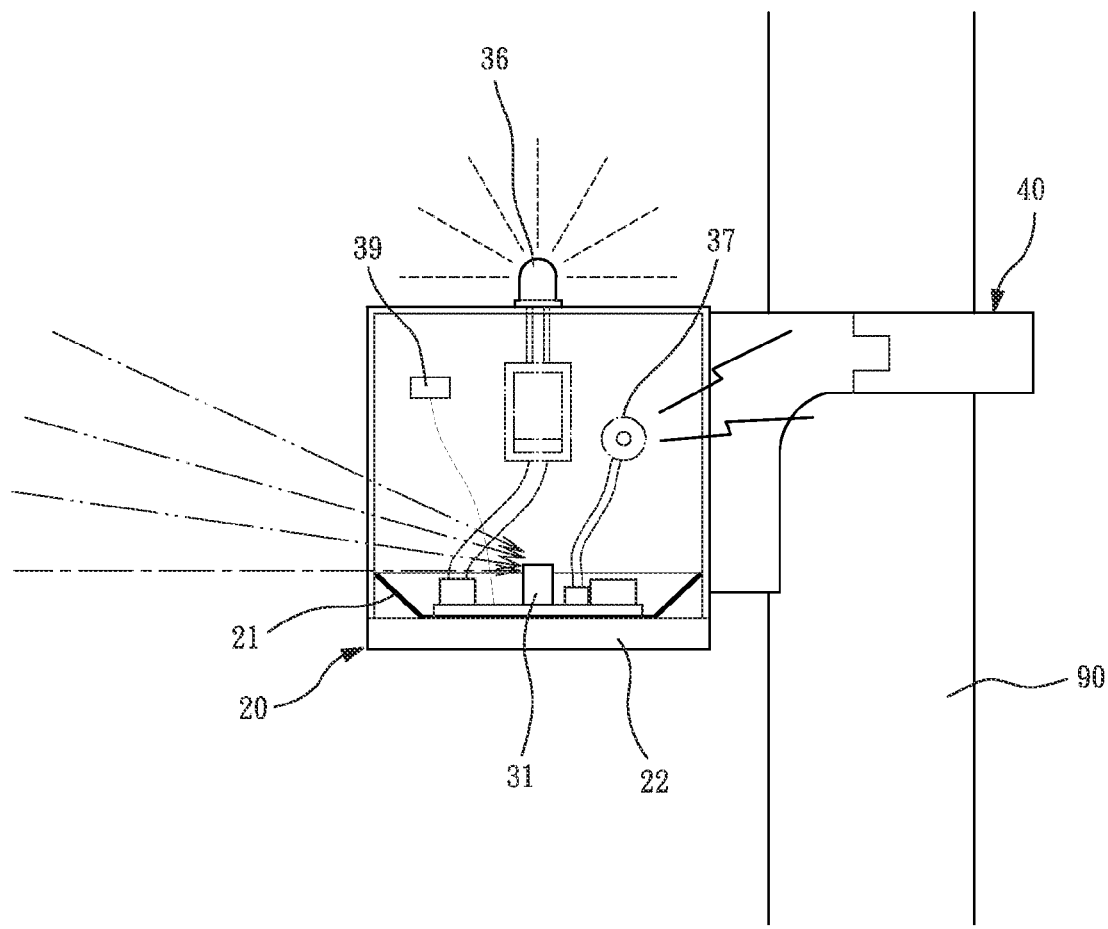
FIG. 13 is a schematic view illustrating an identification signal transmitted from an RF transmitter is received by a receiver.

Referring to FIGS. 12 and 13, when the injection site of the patient is moved by the patient raising up the hand or making an improper movement so as to make the vertical distance between the injection site and the drip chamber 91 less than the predetermined distance, the RF receiver 31 is now capable of receiving the identification signal transmitted from the RF transmitter 12 and the light indication drive circuit 34 and the sound warning drive circuit 35 respectively drive the light emitter 36 and the buzzer 37 to give off lighting and sound warnings to remind lowering the injection site or lifting up the intravenous drip pole in order to avoid the vertical distance between the injection site and the intravenous drip being excessively short that might cause reverse flow and to protect the patient from vein reverse blood flow and jamming caused by undesired raising of the patient's hand.

When the patient makes the injection site located in the safe zone below the RF receiver 31 again, the present invention automatically releases the warning.

For patients who suffer constrained mobility, poor memory, poor eyesight, and poor hearing, they may not be able to lower down the injection site or lift up the intravenous drip pole even when the light emitter 36 and the buzzer 37 continuously give off lighting and sound warnings, a nurses or the family members may press down or operate the shut-down switch 39 to directly release the lighting and sound warnings.

For improved foolproof effect, the decoder IC 322, upon receiving the identification signal from the transmitter unit 10, issues a high level signal to an input pin P1.0 of the single-chip 33 and the single-chip 33 activates a 10-second delay program. If the high level signal is persistent for more than 10 seconds, then the single-chip 33 supplies, through an output pin P2.0, the drive signal to the light indication drive circuit 34 and the sound warning drive circuit 35 to generate the warning signals; otherwise, the high level signal disappears after lo seconds, then it is treated as an erroneous operation and a determination based on the identification signal is re-done again.

The present invention provides advantageous efficacies, including reducing the chance of re-insertion of a retaining needle, improving positive attendant-patient relationship, and lowering down the time and cost of medical caring.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. An automatic sensing and warning device for placing an intravenous drip, comprising:
a transmitter unit, which comprises an encoder circuit and a radio frequency (RF) transmitter that are electrically connected, the encoder circuit comprising a first switch and an encoder integrated circuit (IC) for setting an identification signal of the transmitter unit, wherein the RF transmitter is operable to transmit out the identification signal and the transmitter unit is adapted to attach to an injection site on a hand of a person;

a blocking unit, which comprises a blocking member and a seat, the blocking member being made of a metallic material and mounted on the seat, the seat being adapted to attach to an intravenous drip pole to be substantially perpendicular to the intravenous drip pole, so as to block the identification signal transmitted from the RF transmitter located in one given range of the seat;

a receiver unit, which is mounted to the blocking unit, the receiver unit comprising an RF receiver, a decoder circuit, at least one drive circuit, and at least one warning device, the RF receiver being operable to receive the identification signal transmitted from the RF transmitter located in another one given range of the seat, the decoder circuit being coupled to the RF receiver, the drive circuit being coupled to the decoder circuit, the warning device being coupled to the drive circuit, the decoder circuit comprising a second switch and a decoder IC; and a fixing device, which supports the blocking unit and the receiver unit and is adapted to mount to the intravenous drip pole;

wherein the blocking member comprises a piece of disk-like tin foil.

2. The automatic sensing and warning device for placing an intravenous drip according to claim 1, wherein the encoder circuit and the RF transmitter of the transmitter unit are mounted on a first circuit board.

3. The automatic sensing and warning device for placing an intravenous drip according to claim 1, wherein the transmitter unit is mounted to a hand ring that is provided with hook and hoop fastening strips in order to allow the hand ring to attach the transmitter unit to the injection site of the hand.

4. The automatic sensing and warning device for placing an intravenous drip according to claim 1, wherein the decoder circuit is coupled to a single-chip, and the single-chip comprises a time delay module for a delay of time in issuing a drive signal to the drive circuit, so as to delay driving the warning device.

5. The automatic sensing and warning device for placing an intravenous drip according to claim 1, wherein the drive circuit comprises a light indication drive circuit and a sound warning drive circuit, the light indication drive circuit being electrically connected to a light emitter, the sound warning drive circuit being electrically connected to a buzzer.

6. The automatic sensing and warning device for placing an intravenous drip according to claim 1, wherein the RF receiver, the decoder circuit, and the drive circuit the receiver unit are mounted on a second circuit board.

7. The automatic sensing and warning device for placing an intravenous drip according to claim 1, wherein the fixing device comprises a C-clip.

8. The automatic sensing and warning device for placing an intravenous drip according to claim 1, wherein the receiver unit comprises a shut-down switch, which is operable to cut off a single transmission circuit of the receiver unit.

* * * * *